(12) United States Patent
McMahon et al.

(10) Patent No.: US 6,458,094 B1
(45) Date of Patent: Oct. 1, 2002

(54) DISPOSABLE TIP FOR BODY CAVITY IRRIGATION SYSTEM

(75) Inventors: Michael McMahon, Syracuse, NY (US); Stephen Burnett, Locke, NY (US); James A. Caryl, Camillus, NY (US); William R. Witkowski, Marcellus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 16 days.

(21) Appl. No.: 09/832,609

(22) Filed: Apr. 11, 2001

(51) Int. Cl.[7] .................................................. A61M 1/00
(52) U.S. Cl. ........................ 604/35; 604/38; 604/150
(58) Field of Search ........................... 604/27, 28, 30, 604/32, 33, 35, 39, 43, 500, 514, 118, 131, 150, 38; 601/155; 236/87, 90

(56) References Cited

U.S. PATENT DOCUMENTS

| | | |
|---|---|---|
| 604,178 A | 6/1898 | Ferguson |
| 785,524 A | 3/1905 | Shea |
| 989,839 A | 4/1911 | Fowler |
| 1,719,152 A | 7/1929 | Watson |
| 2,112,145 A | 3/1938 | Courtney |
| 2,208,031 A | 7/1940 | Hooper |
| 2,525,419 A | 10/1950 | Mellinger et al. |
| 2,626,524 A | 1/1953 | Harman |
| 2,645,116 A | 7/1953 | Baxter |
| 3,142,297 A | 7/1964 | Attebery |
| 3,669,101 A | 6/1972 | Kleiner |
| 3,682,176 A | 8/1972 | Kelson |
| 3,696,996 A | 10/1972 | Lloyd et al. |
| 3,769,976 A | 11/1973 | Victory |
| 3,788,305 A | 1/1974 | Schreiber |
| 3,916,895 A | 11/1975 | Davis, Jr. |
| 3,971,375 A | 7/1976 | Hill |
| 4,149,315 A | 4/1979 | Page, Jr. et al. |
| 4,206,756 A | 6/1980 | Grossan |
| 4,258,714 A | 3/1981 | Leopoldi et al. |
| 4,282,867 A | 8/1981 | Dutoit |
| 4,284,078 A | 8/1981 | Pace |
| 4,303,195 A | 12/1981 | Hashimoto et al. |
| 4,413,633 A | 11/1983 | Yanda |
| 4,437,574 A | 3/1984 | Ruklic |
| 4,738,375 A | 4/1988 | Rosen et al. |

(List continued on next page.)

*Primary Examiner*—Lesley D. Morris
*Assistant Examiner*—John Fristoe
(74) *Attorney, Agent, or Firm*—Wall Marjama & Bilinski LLP

(57) ABSTRACT

A disposable insertion tip for a body cavity cleaning or irrigation device includes at least one tear strip. Once attached to the cleaning device, the insertion tip is sealingly locked in a predetermined position permitting liquid to be dispensed into a body cavity and used liquid to be returned from the body cavity through respective interior chambers provided in the insertion tip. The tip cannot be removed without first tearing the tear strip, which once torn, disables the sealing capability of the tip relative to the cleaning device. The insertion tip is preferably made from a transparent material which permits a user to view the efficacy of a cleaning procedure and to note when removal of the tip is required.

55 Claims, 2 Drawing Sheets

U.S. PATENT DOCUMENTS

| | | |
|---|---|---|
| 4,819,825 A | 4/1989 | Landis |
| 4,893,634 A | 1/1990 | Kulik et al. |
| 4,957,483 A | 9/1990 | Gonser et al. |
| 5,024,378 A | 6/1991 | Bergmann et al. |
| 5,046,486 A * | 9/1991 | Grulke et al. ............... 601/161 |
| 5,241,714 A | 9/1993 | Barry |
| D340,112 S | 10/1993 | Zeman |
| 5,265,959 A | 11/1993 | Meltzer |
| 5,269,750 A * | 12/1993 | Grulke et al. ............... 362/804 |
| 5,302,028 A | 4/1994 | Carey |
| 5,304,003 A | 4/1994 | Winninger |
| 5,309,899 A | 5/1994 | Ginsberg |
| 5,364,343 A | 11/1994 | Apolet et al. |
| 5,460,604 A * | 10/1995 | Arnett et al. ................. 604/35 |
| 5,527,275 A * | 6/1996 | Ginsberg .................... 601/155 |
| 5,642,825 A | 7/1997 | Wohlgemuth |
| 5,685,851 A * | 11/1997 | Murphy et al. ............. 601/155 |
| 5,772,616 A | 6/1998 | Competiello et al. |
| 5,944,711 A | 8/1999 | Pender |
| 5,967,409 A | 10/1999 | Benedict |
| RE36,729 E | 6/2000 | Luch et al. |
| 6,179,807 B1 * | 1/2001 | Henniges et al. ............. 604/35 |

\* cited by examiner

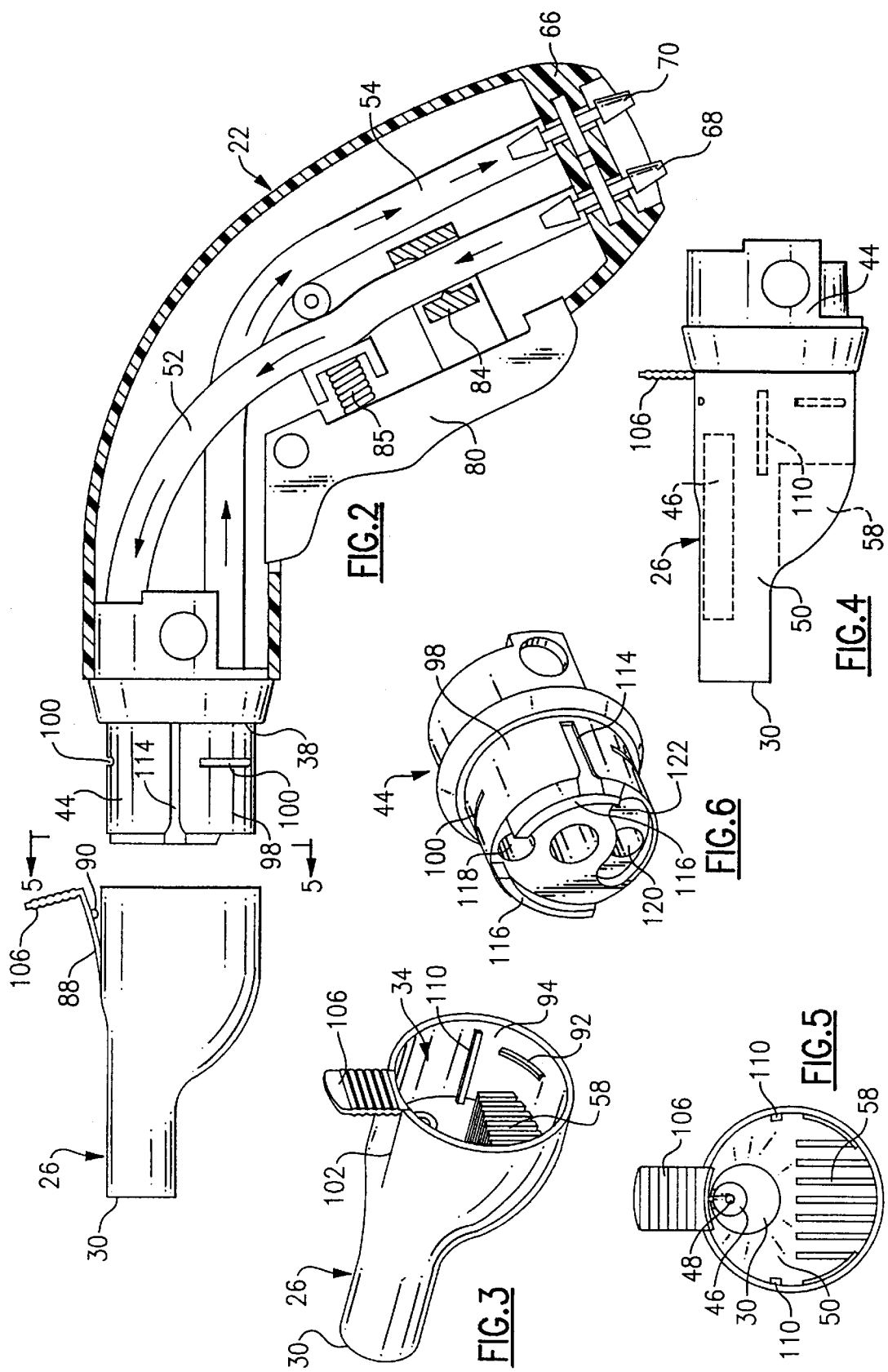

DISPOSABLE TIP FOR BODY CAVITY IRRIGATION SYSTEM

FIELD OF THE INVENTION

The invention relates to the field of irrigation systems, and more particularly to a disposable insertion tip for an irrigation system used for cleaning the ears or other body cavities.

BACKGROUND OF THE INVENTION

Irrigation syringes are routinely known for cleaning human body cavities, such as the ears. Most commonly, a flexible and depressible bulb is fitted to a nozzle through which fluid (water) can be discharged into the ear canal of a patient.

Bulb-type irrigation devices have several drawbacks. First, the bulb capacity limits the effective usage of the device given that the bulb can retain only a relatively small quantity of water. Often and to fully irrigate a patient's ear, the flexible bulb may have to be refilled a number of times.

Second, the pressure of the water exiting the nozzle of the device and impinging upon the ear canal can not be readily controlled in a reliable manner. This lack of control produces variable results and can in turn, cause pain and injure a patient due to the sensitivity of the tympanic membrane.

Other known irrigation devices incorporate mechanical pumps which interconnect a fluid reservoir with the nozzle. These devices are capable of producing pulsating streams of water ejecting from the nozzle opening for a sustained period of time. Besides being rather bulky and cumbersome, however, the above devices also produce sufficient amounts of both vibration and noise commonly associated with mechanical pumps. Each result is annoying and undesirable in a doctor's office or similar setting. A further consideration concerning the above referred to devices is that the volume of the fluid reservoir, though greater than that of the flexible bulb-type devices, must also be refilled at periodic intervals.

More recently, an irrigation device such as described by U.S. Pat. No. 5,685,851, to Murphy et al., the entire contents of which are herein incorporated, includes a pressure regulator unit having an inlet port which is fluidly connected to a faucet and a discharge port which is connected to an irrigation syringe. The irrigation syringe is hand-grippable and includes a push button control which selectively restricts the flow of liquid from the pressure regulator unit. The pressure regulator unit permits connection to a continuous water source (e.g., the faucet) and includes a number of retained components including a flow limiting orifice in a supply chamber, a defined air buffer, and a check valve, in order to effectively control the pressure of water supplied by the faucet to produce a smooth and consistent continuous flow to the irrigation syringe and the patient.

A further refinement is described in copending U.S. patent application Ser. No. 09/630,884 filed Aug. 2, 2000, the entire contents of which are also herein incorporated by reference. This body cavity irrigation system also includes an irrigation syringe defined by a hand piece and an insertion tip or nozzle. The hand piece is connected to a pressure regulator unit which is similarly connected to a faucet or other continuous liquid supply and further includes inlet and return lines which are fluidly connected to an inlet cavity and an outlet cavity, respectively, provided in the insertion tip. The inlet cavity permits water to be discharged into the ear, while the outlet cavity collects waste water after it has been discharged into the ear, the waste water being returned via the return channel to a basin or sink for disposal.

It is generally preferred for health and sanitary reasons that an insertion tip, such as described immediately above, be used only for a single patient and then disposed of thereafter. For these reasons, there is a compelling need to insure that the insertion tip cannot effectively be reused.

SUMMARY OF THE INVENTION

It is a primary object of the present invention to overcome the above noted problems of the prior art.

It is another primary object of the present invention to provide a disposable insertion tip for a body cavity cleaning system, such as for irrigating the ears, wherein the insertion tip can only be used a single time; that is, the tip is ineffective after removal from an irrigation syringe.

Therefore and according to a preferred aspect of the present invention, there is provided a body cavity cleaning device, said device including a hand piece which receives a supply of liquid under pressure for cleaning a body cavity and an insertion tip. The insertion tip is releasably attachable to one end of the hand piece and includes release means for selectively releasing the insertion tip from the hand piece, wherein engagement of the release means prevents effective reuse of the insertion tip in conjunction with the body cavity cleaning device.

In addition, the insertion tip preferably includes a pair of interior chambers fluidly interconnected to the hand piece including an inlet chamber which discharges liquid into a body cavity and an outlet chamber which returning used liquid from the body cavity to a return line of the hand piece.

Preferably, the release means includes at least one tear strip which, when torn, prevents the insertion tip from being usefully reattached to the hand piece. Therefore, the insertion tip is disposable and is effective only for a single patient. The insertion tip preferably includes at least one circumferential interior protrusion or recess which provides locking engagement with a corresponding recess or protrusion provided on an engagement portion of the hand piece. The tear strip must be employed in order to unlock and remove the insertion tip from the hand piece. Once the tear strip has been removed, the sealing capability of the insertion tip with the hand piece is disabled, and the insertion tip can no longer be effectively attached to the cleaning device. Moreover, the mechanical integrity of the attachment of the tip, as well as the ability of the tip to resist camming or twisting forces, is markedly compromised after the tear strip has been engaged.

Preferably, the tear strip includes at least one weakened area used in combination with a pull tab which facilitates tearing of the strip relative to the insertion tip. In addition, the tip includes at least one alignment member to insure a proper angular orientation, relative to the and piece, when the tip is initially attached thereto.

As noted, the insertion tip includes a pair of adjacent interior chambers whereby liquid from a continuous fluid source, such as a faucet, is discharged through a first or inlet chamber in order to irrigate the body cavity (e.g., ear). An adjacent second or outlet chamber returns waste water discharged away from the body cavity for disposal. The inlet chamber includes a tip orifice sized to discharge liquid at a predetermined rate in relation to a distal tip orifice of the insertion tip. Preferably, the tip orifice of the inlet chamber is off center relative to the distal tip opening of the insertion tip to maximize the passageway for flushed particulate, such as cerumen.

The second or outlet chamber further includes at least one filter for capturing particulates (e.g., cerumen) contained in the waste water. Preferably, the insertion tip is made from a flexible transparent or translucent plastic material to permit a doctor or other user to verify that an effective cleaning procedure has been performed successfully. Furthermore, the filter is designed to be used one time, given that the filter will retain only a predetermined amount of particulate.

According to another preferred aspect of the invention there is provided, in combination, a disposable insertion tip for use with a body cavity cleaning device, said device including a handgrippable syringe which receives a supply of liquid under pressure for cleaning the body cavity and a return line for receiving used liquid and particulates from the body cavity. The insertion tip is releasably attachable to the syringe and includes release means for selectively releasing said insertion tip from said syringe, wherein engagement of said release means prevents effective reuse of said insertion tip in conjunction with said handgrippable syringe.

Preferably, the body cavity cleaning device is an ear irrigation apparatus in which the insertion tip is locked onto the syringe during assembly, the release means including at least one tear strip provided on the insertion tip.

According to yet another preferred aspect of the present invention, there is provided a disposable insertion tip which is releasably attachable to a body cavity cleaning device. The insertion tip includes release means for preventing the insertion tip from being removed from the cleaning device without disabling the insertion tip, thereby preventing reuse thereof The insertion tip preferably includes a pair of interior chambers fluidly interconnected to the cleaning device which discharges liquid to a body cavity and removes waste liquid from the body cavity, respectively.

The release means unlocks the tip relative to a handpiece of the cleaning device onto which the tip is initially mounted and preferably includes at least one tear strip. Once the tear strip has been torn, the tip cannot effectively be reattached to the cleaning device rendering the tip useless. Furthermore, the tip cannot be removed from the handpiece without first employing the tear strip.

According to still another preferred aspect of the present invention, there is provided a method for preventing the reuse of a used insertion tip relative to a body cavity irrigation device, said method comprising the steps of attaching a insertion tip to said insertion device; pulling a frangible tear strip of said insertion tip; and removing the insertion tip from the device. The tear strip effectively disables the sealing capability of the insertion tip relative to the irrigation device once the tear strip has been torn and thereby prevents the tip from being successfully reused.

The attaching step includes the step of locking the insertion tip into engagement with the syringe wherein the insertion tip cannot be removed without first tearing the tear strip.

According to yet another preferred aspect of the present invention, there is provided a disposable insertion tip for use with a body cavity cleaning device, said insertion tip being adapted for releasable attachment to said device and including release means for selectively releasing the insertion tip from the cleaning device. The release means, upon engagement thereof, prevents effective reuse of said insertion tip in conjunction with the device. The tip is capable of circulating liquid to and liquid and particulates from a body cavity, said tip further including means for filtering the particulates. Preferably, the filtering means is provided in a return or outlet chamber of the insertion tip.

An advantage of the present invention is that a disposable insertion tip is provided which cannot be removed from a body cavity cleaning device, such as for ear irrigation, without disabling same.

A further advantage of the present invention is that the tear strip must be employed in order to release the insertion tip from the cleaning device. According to a preferred embodiment, the insertion tip, when initially attached to the syringe, effectively locks the tip in place. Therefore, any forced removal of the tip will require significant force and cause tearing of the tear strip, even when the strip is not first deliberately torn by the user. Therefore single use of an insertion tip, as described by the present invention, upon removal from a body cavity cleaning device, is virtually guaranteed.

Yet another advantage of the present invention is that a disposable tip such as described herein provides an effective fluid seal until the tear strip is acted upon. Use of the tear strip thereafter seriously destroys the sealing capability of the insertion tip should a user attempt to reattach a used tip to the irrigation device.

Yet another advantage of the present invention is that the tip is preferably made from a soft moldable plastic which provides comfort for a patient when the tip is inserted into a body cavity such as the ear. The tip, further being made from a translucent or transparent material also permits a user to visually note the efficacy of a cleaning procedure and to note when the filter is clogged, requiring the need for removal of the tip from the syringe. The described tip is also cost effective to manufacture, easy to use, and is efficient in design.

These and other objects, features, and advantages will become apparent from the following Detailed Description which should be read in conjunction with the accompanying drawings.

BRIEF DESCRIPTION OF THE DRAWINGS

FIG. 2 is a sectional view of an irrigation syringe of the body cavity irrigation system of FIG. 1, including the insertion tip as it is removed from a handpiece;

FIG. 3 is a rear perspective view of the insertion tip of FIG. 2;

FIG. 4 is a side view of the insertion tip of FIGS. 2 and 3;

FIG. 5 is a rear view of the insertion tip of FIGS. 2–4; and

FIG. 6 is a front perspective view of the engagement portion of the handpiece of FIG. 2.

DETAILED DESCRIPTION

Figure 1:
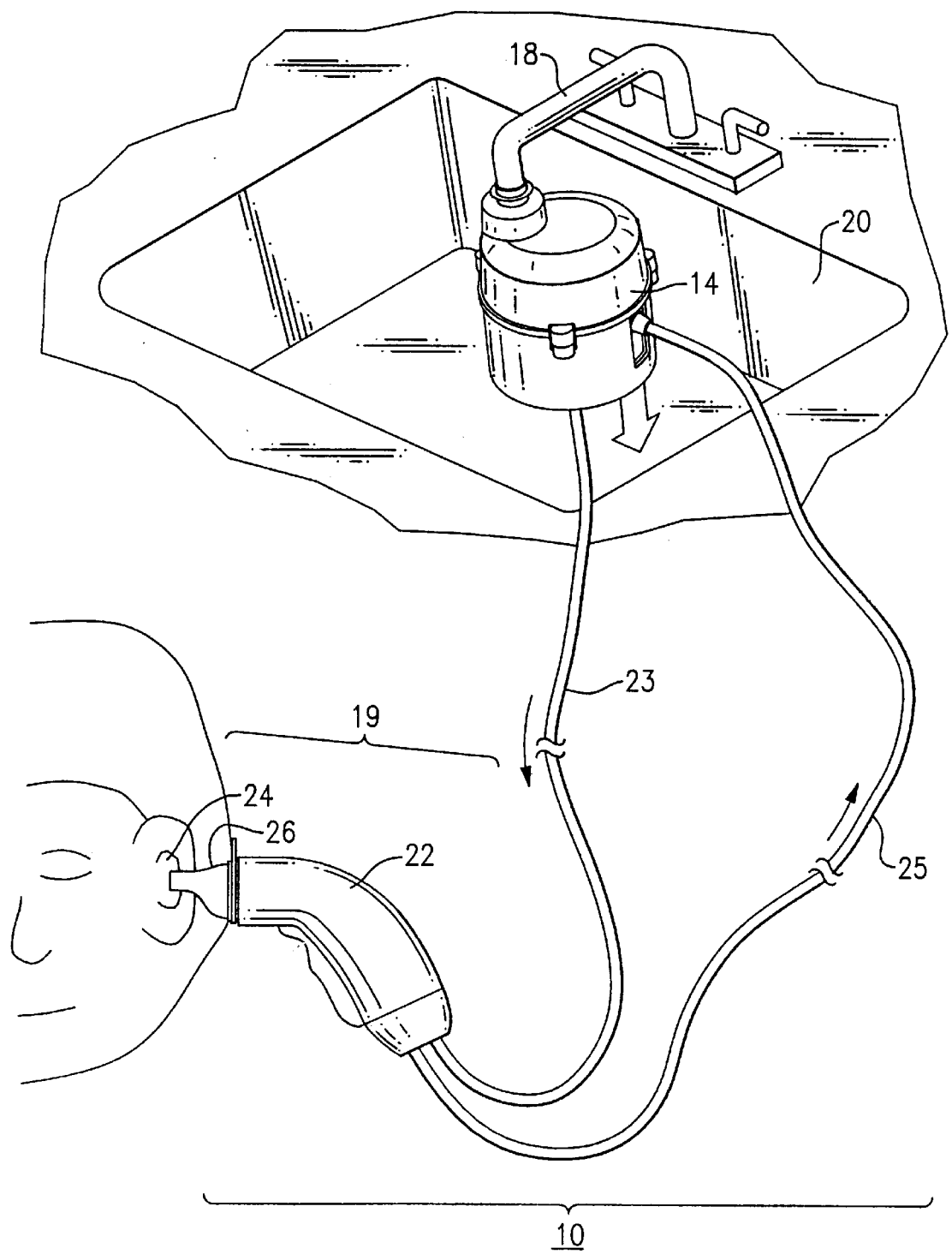
FIG. 1 is a perspective view of a body cavity irrigation system using a disposable insertion tip made in accordance with a preferred embodiment of the present invention.

The following description specifically relates to a disposable (e.g. single patient) use insertion tip for an ear wash or irrigation system according to a preferred embodiment. It will, however, be readily apparent to one of sufficient skill in the field that there are many variations and modifications possible which embody the inventive aspects that are described and claimed herein. For example, and though the present device is directed to ear irrigation, it should be readily apparent that the inventive concepts described herein can be also be applied to the cleaning of other body cavities, including but not limited to the anus, vagina, nose, and mouth. Furthermore, the system can also be used for other suitable purposes, such as the irrigation of wounds.

In passing, it should also be noted that the term "syringe" as defined herein, refers specifically to any device which is capable of injecting a fluid. In addition, other terms are used throughout the description which provide a frame of reference with respect to the accompanying drawings, such as "top", "bottom", "lower", "upper", "distal", "proximal" and the like. These terms are not intended to be limiting of the present invention as claimed, except where specifically described as such.

Turning to FIG. 1, the irrigation based ear-wash system 10 according to this embodiment includes a pressure regulator unit or housing 14 which is connected to a faucet 18 or other suitable continuous fluid supply that delivers liquid under pressure. The housing 14 is further connected to an irrigation syringe 19. In brief, the irrigation syringe 19 is connected to the housing 14 by means of an inlet line 23, which delivers liquid from the housing to the syringe 19, and a return line 25 through which discharged liquid is collected and then eliminated through the housing and subsequently into a sink 20.

Referring to FIGS. 1 and 2, the irrigation syringe 19 includes a handgrippable handpiece 22 and a syringe or insertion tip 26 which is releasably attached to a distal end 38 of the handpiece. In this embodiment, the handpiece 22 is defined by a hand-grippable pistol-shaped body made preferably from a lightweight injection-molded plastic having a distal opening accessing an engagement portion 44 which receives the insertion tip 26.

The insertion tip 26 according to this embodiment is formed from a flexible transparent injection-molded plastic, the tip having a distal end which is capable of being inserted a predetermined distance into the ear canal 24, FIG. 1, of a patient. The insertion tip 26 is substantially hollow, including a distal tip opening 30 and an open proximal end 34. A pair of adjacent cavities 46, 50, are positioned within the tip interior, which when assembled to the distal end 38 of the handpiece 22 are aligned with and positioned through barbs (not shown) or other means in fluid communication with the distal ends of respective supply and return fluid channels 52, 54. The inlet cavity 46 of the insertion tip 26 is defined by a narrow tubular member having an inlet diameter extending to a distal tip opening 48. The diameter of the distal tip opening 48 is considerably smaller than that of the inlet diameter to control the amount and pressure of liquid being dispensed through the distal tip opening 30 of the insertion tip. The return cavity 50 is substantially larger than the inlet cavity 46 and includes a filter 58 having a series of parallel spaced ribs, the filter being designed to trap removed cerumen (not shown) contained in waste liquid which has already been dispensed into the ear canal 24, FIG. 1. Preferably, the tubular member defining the inlet cavity 46 is offset relative to the distal tip opening 48 in both the vertical and horizontal directions in order to maximize the return passageway for flushed cerumen or other returned particulate.

The proximal ends of the flexible fluid channels 52, 54 are attached to respective barbs of inlet and outlet couplings 68, 70 provided at the proximal end 66 of the handpiece 32 and in fluid communication with the inlet and return lines 23, 25, FIG. 1, respectively.

The handpiece 32 includes a trigger 80 which enables a clamp 84 to pinch off the flexible inlet fluid channel 52, the clamp being biased by a spring 85. Depression of the trigger 80 releases the pressure of the clamp 84 upon the fluid channel 52 to selectively permit fluid flow from the housing 14 for dispensing thereof. Specific details relating to each of the above features are provided in U.S. application Ser. No. 09/630,884, previously incorporated by reference.

The insertion tip 26, as shown in FIGS. 2 and 4, is releasably attached onto the exterior surface 98 of the engagement portion 44 of the handpiece 32. As previously noted, the insertion tip 26 is made from a flexible plastic material, the tip being made slightly smaller in diameter than that of the engagement portion 44 of the handpiece 32 to create a tightly sealed interference fit.

Referring to FIGS. 3 and 5, the insertion tip 26 includes a predetermined number of circumferential tabs or protrusions 90, 92 that are provided on an interior surface 94. In the present embodiment, three (3) spaced protrusions are provided, though it will be apparent from the discussion that this parameter can easily be varied. According to this embodiment, one of the protrusions 90 is provided along the entire circumferential span of the tear strip 88, while the remaining two protrusions 92 are each centered approximately 135 degrees clockwise and counterclockwise, respectively, relative to the tear strip protrusion 90.

The protrusions 90, 92 collectively cover only a circumferential portion of the interior surface 94 of the insertion tip 26. According to the present embodiment, the protrusions 90, 92 each cover approximately a 30 degree segment, though this parameter can also be easily varied, wherein each of the protrusions are disposed commonly within a circumferential plane extending a predetermined axial distance from the proximal end 34 of the tip 26.

The exterior surface 98 of the engagement portion 44 of the handpiece 32, according to this embodiment includes a corresponding number of recesses 100 sized and disposed relative to one another for retaining the protrusions 90, 92 provided on the interior surface 94 of the insertion tip 26.

As described herein, the insertion tip 26 includes selectively engageable release means for permitting removal from the handpiece 22. Preferably, a frangible tear strip 88 permits removal of the insertion tip 26 after assembly of same to the hand piece 22 and furthermore prevents effective reuse of the tip after the tear strip has been utilized for removal thereof.

The tear strip 88 is further defined by a pair of parallel longitudinal weakened areas 102 (only one being shown in FIG. 3) as well as a radially extending pull tab 106. The weakened areas 102 according to this embodiment are spanned circumferentially by the protrusion 90 and extend over an axial portion of the insertion tip 26.

According to this embodiment, the insertion tip 26 further includes a pair of axial alignment rails or members 110, each of which are angularly disposed on the interior surface 94. A pair of corresponding receiving slots 114 provided on the exterior surface 98 of the engagement portion 44 in conjunction with the alignment members 110 assist in angularly aligning the insertion tip 26 so as to prevent mispositioning of the tear strip 88 and each of the inlet and outlet chambers 46, 50 relative to the corresponding inlet and outlet channels of the hand piece 22.

Referring to the Figs. in general and in use, the insertion tip 26 is mounted onto the exterior surface 98 of the engagement portion 44 of the handpiece 32 such that each of the protrusions 90, 92 and the recesses 100 are aligned with one another. The protrusions 90, 92 and recesses 100 are disposed in conjunction with the rails 110 and the slots 114 in order that the inlet and outlet channels 52, 54 of the handpiece 32 are properly aligned with the inlet and return chambers 46, 50 of the insertion tip 26.

After aligning circumferentially with the engagement portion 44 of the handpiece 32, the insertion tip 26 is pushed axially toward the proximal end 66 of the handpiece 32 until the protrusions 90, 92 are press-fitted into the recesses 100, thereby effectively locking the tip in place and permitting the patient's ears to be cleaned using the irrigation system 10. In this position, the ribs of the filter 58 are in substantial contact with the distal end of the engagement portion 44. More particularly, and referring to FIG. 6, the distal end of the engagement portion 44 further includes a pair of annular protrusions 116 and a pair of openings, namely a discharge opening 118 and a return opening 120 which permit liquid to enter the inlet cavity 46 and discharges waste water passing through the filter 58 from the return cavity 50, respectively. According to this embodiment, the return opening 120 further includes a recess 122 which assists in directing return liquid given the direct engagement of the engagement portion 44 with the filter 58.

Once the protrusions 90, 92 have engaged the recesses 100, the insertion tip 26 is effectively locked into position and the irrigation system 10 can be used to clean the ears of a patient.

Water is dispensed selectively using the trigger 80 of the handpiece 22. The frustoconical shape of the insertion tip 26 permits placement thereof a predetermined distance into the ear canal 24, FIG. 1, the tip being made from a soft flexible plastic producing little discomfort to the patient. As noted above, waste water is returned to a basin or sink via the return channel 54 of the handpiece 22 from the return cavity of the tip 26. As noted, the insertion tip 26 is sealingly engaged with the engagement portion 44 of the handpiece to prevent leakage upon initial assembly.

Following a ear cleaning procedure, the physician or other user can pull the pull tab 106 toward the distal tip opening 48 of the insertion tip 26, tearing the tear strip 88 along the axial weakened lines 102. The preceding permits the insertion tip 26 to be released axially from the handpiece 32, as shown in FIG. 2.

Preferably, the insertion tip 26 cannot be removed from the hand piece 22 without first tearing the tear strip 88 due to the tight interference seal fit of the tip against the exterior surface 98 of the engagement portion 44. Any attempt to twist or otherwise remove the insertion tip 26 without first deliberately employing the tear strip 88 will cause the preweakened areas 102 of the tear strip to engage an edge of at least one of the annular protrusions 116 of the engagement portion 44 of the handpiece 22. Once so engaged, the tear strip 88 is caused to be torn.

As noted, once the tear strip 88 has been engaged, the insertion tip 26 cannot effectively be reused in that an effective seal can no longer be made with the handpiece 22. As a result, any attempt to reattach a used insertion tip 26 will provide a loose non-sealed fit of the protrusions 90, 92 with the recesses 100 and, in any event, will cause leakage of return waste fluid from the return cavity 50, rendering the tip literally ineffective for cleaning thereafter. Moreover, the mechanical integrity of the attachment of the insertion tip 26, as well as the ability of the tip to resist twisting or camming forces is also markedly compromised.

Additionally, and in the event one attempts to leave the insertion tip 26 on the handpiece 22 without removal between patients, the tip will eventually clog due to excessive amounts of cerumen (not shown) blocking the return opening 120, also necessitating removal of the tip.

PARTS LIST FOR FIGS. 1–6

10 irrigation system
14 housing
18 faucet
19 syringe
20 sink
22 handpiece
23 inlet line
24 ear canal
25 return line
26 insertion tip
30 distal tip opening
34 proximal end—tip
38 distal end
44 engagement portion
46 inlet cavity
48 distal tip opening—inlet cavity
50 return cavity
52 fluid channel
54 fluid channel
58 filter
60 distal end—engagement portion
66 proximal end
68 inlet coupling
70 return coupling
80 trigger
84 clamp
85 torsion spring
88 tear strip
90 protrusion
92 protrusion
94 interior surface
98 exterior surface
100 recesses
102 weakened areas
106 pull tab
110 alignment members
114 slots
116 protrusions
118 discharge opening
120 return opening
122 recess It will be readily apparent that other modifications and variations are possible within the intended scope of the following claims. For example, and though the primary embodiment included a single axial tear strip, other types of release mechanisms, such as multiple axial tear strips or a circumferential tear strip, could be utilized to perform a similar function.

We claim:

1. A body cavity cleaning device, including a handpiece which receives a supply of liquid under pressure for cleaning a body cavity and an insertion tip, said tip being releasably attachable to said handpiece and including release means for selectively releasing said insertion tip from said hand piece wherein engagement of said release means prevents effective reuse of said insertion tip, said insertion tip further including a pair of interior chambers, an inlet chamber for discharging liquid into the body cavity from said handpiece and an outlet chamber for returning used liquid from the body cavity to a return line of said handpiece.

2. A device according to claim 1, wherein said body cavity cleaning device is an ear irrigation apparatus.

3. A device according to claim 1, wherein said release means includes at least one tear strip provided on said insertion tip.

4. A device according to claim 1, including locking means for locking said insertion tip to said handpiece.

5. A device according to claim 4, wherein said locking means includes at least one circumferential protrusion provided on one of the interior of said insertion tip and an exterior surface of an engagement portion of said handpiece for engaging at least one corresponding recess sized for receiving said at least one protrusion on the other of said insertion tip and said engagement portion.

6. A device according to claim 5, wherein said insertion tip includes at least two protrusions, each protrusion sized for engaging a corresponding recess provided on said engagement portion of said handpiece.

7. A device according to claim 5, wherein at least one protrusion is provided on the interior of said insertion tip on said release means.

8. A device according to claim 3, wherein said at least one tear strip includes at least one weakened area permitting the tear strip to be torn.

9. A device according to claim 1, including at least one filter disposed in said outlet chamber.

10. A device according to claim 1, including alignment means for angularly positioning said insertion tip relative to said handpiece.

11. A device according to claim 10, wherein said handpiece includes said return line and an inlet line, said alignment means permitting said inlet line and return line of said handpiece to be aligned with the inlet and outlet chambers of said insertion tip.

12. A device according to claim 1, wherein said inlet chamber includes a discharge opening, said discharge opening being axially offset relative to a primary axis of a discharge opening of said insertion tip.

13. A device according to claim 1, wherein said inlet chamber includes a discharge opening, said discharge opening having a diameter which is smaller than that of the remainder of said inlet chamber and a discharge opening of said insertion tip.

14. A device according to claim 1, wherein said handpiece includes means for engaging said release means when an attempt is made to remove the insertion tip from said handpiece without first deliberately engaging said release means.

15. A device according to claim 1, wherein said insertion tip is made from a transparent material to permit a user to visually inspect a cleaning procedure.

16. In combination, a disposable insertion tip for use with a body cavity cleaning device, said device including a handgrippable syringe which receives a supply of liquid under pressure for cleaning the body cavity and includes a return line for receiving used liquid and particulates from the body cavity, said insertion tip being releasably attachable to said syringe and including engageable release means for selectively releasing said insertion tip from said syringe, wherein engagement of said release means prevents effective reuse of said insertion tip in conjunction with said handgrippable syringe.

17. A combination according to claim 16, wherein said body cavity cleaning device is an ear irrigation apparatus.

18. A combination according to claim 16, wherein said release means includes at least one tear strip provided on said insertion tip.

19. A combination according to claim 16, including means for locking said insertion tip to said syringe.

20. A combination according to claim 19, wherein said locking means includes at least one circumferential protrusion provided on one of the interior of said insertion tip and an engagement portion of said insertion for engaging at least one corresponding recess sized for receiving said at least one protrusion on the other of said insertion tip and said engagement portion.

21. A combination according to claim 20, wherein said insertion tip includes at least two protrusions, each protrusion sized for engaging a corresponding recess provided on said engagement portion of said syringe.

22. A combination according to claim 21, wherein at least one protrusion is provided on the interior of said insertion tip on said release means.

23. A combination according to claim 18, wherein said at least one tear strip includes at least one weakened area which permits tearing thereof.

24. A combination according to claim 16, wherein said insertion tip includes a pair of chambers, an inlet chamber for liquid entering the body cavity from said syringe and an outlet chamber for returning used liquid from the body cavity to said insertion along a return line.

25. A combination according to claim 24, including at least one filter for trapping particulates, said at least one filter being disposed in said return chamber.

26. A combination according to claim 16, wherein said insertion tip includes at least one filter for trapping particulates.

27. A combination according to claim 24, including alignment means for angularly positioning said insertion tip relative to said syringe.

28. A combination according to claim 27, wherein said syringe includes said return line and an inlet line, said alignment means permitting said inlet line and return line of said syringe to be aligned with the inlet and outlet chambers of said insertion tip.

29. A combination according to claim 24, wherein said inlet chamber includes a discharge opening, said discharge opening being axially offset relative to a primary axis of a discharge opening of said insertion tip.

30. A combination according to claim 24, wherein said inlet chamber includes a discharge opening, said discharge opening having a diameter which is smaller than each of the remainder of said inlet chamber and a discharge opening of said insertion tip.

31. A combination according to claim 16, wherein said syringe includes means for engaging said release means if the insertion tip is removed from said syringe without engaging release means.

32. A combination according to claim 16, wherein said tip is made from a transparent material to permit a user to visually inspect a cleaning procedure.

33. A disposable insertion tip which is releasably attachable to a body cavity cleaning device, said insertion tip including release means for preventing said insertion tip from being removed from the cleaning device without disabling said insertion tip so as to prevent reuse thereof.

34. An insertion tip according to claim 33, wherein said release means includes at least one tear strip, which when engaged prevents said insertion tip from being effectively reattached to the device.

35. An insertion tip according to claim 33, including locking means for locking said insertion tip relative to said body cavity cleaning device.

36. An insertion tip according to claim 34, wherein said at least one tear strip includes at least one weakened area permitting tearing thereof.

37. An insertion tip according to claim 33, including a pair of interior chambers, an inlet chamber for liquid entering the body cavity and an outlet chamber for returning used liquid from the body cavity.

38. An insertion tip according to claim 37, including at least one filter disposed in said return.

39. An insertion tip according to claim 33, including alignment means for angularly positioning said insertion tip relative to said cleaning device in a specific operation.

40. An insertion tip according to claim 37, wherein said inlet chamber includes a discharge opening, said discharge opening being axially offset relative to a primary axis of a discharge opening of said insertion tip.

41. An insertion tip according to claim 37, wherein said inlet chamber includes a discharge opening, said discharge opening being narrow relative to the remainder of said inlet chamber and a discharge opening of said insertion tip.

42. An insertion tip according to claim 33, wherein said tip made from a transparent material permitting a user to visually inspect a cleaning procedure.

43. A method for disabling the use of a syringe tip relative to an irrigation syringe, said method comprising the steps of:
  attaching a releasable insertion tip to said syringe;
  using said syringe to irrigate a body cavity;
  pulling a tear strip of said insertion tip to release said tip; and
  removing said insertion tip from said syringe, said tear strip removing a portion of a sealing area relative to said syringe, preventing effective reuse thereof.

44. A method as relative in claim 43, wherein said attaching step includes the step of locking said insertion tip into engagement with said syringe, said insertion tip not being removable without first tearing the tear strip.

45. A method as recited in claim 43, wherein said insertion tip includes at least one filter for trapping particulates and said tip is made from a transparent material, said using step including the step of visually monitoring the condition of said at least one filter to assist in determining when the tip should be removed from said syringe.

46. A disposable insertion tip for use with a body cavity cleaning device, said insertion tip being adapted for releasable attachment to said device and including release means for selectively releasing said insertion tip from said device, wherein said release means upon engagement thereof prevents effective reuse of said insertion tip in conjunction with said device, said tip being capable of circulating liquid to and liquid and particulates from a body cavity, said tip further including means for filtering said particulates.

47. An insertion tip according to claim 46, wherein said release means includes at least one tear strip which when torn prevents said insertion tip from being effectively reattached to the cleaning device.

48. An insertion tip according to claim 46, including locking means for locking said insertion tip relative to said body cavity cleaning device.

49. An insertion tip according to claim 47, wherein said at least one tear strip includes at least one weakened line of material thickness.

50. An insertion tip according to claim 46, including a pair of interior chambers, an inlet chamber for dispensing liquid into a body cavity and a return chamber for returning used liquid from the body cavity.

51. An insertion tip according to claim 50, including at least one filter disposed in said return chamber.

52. An insertion tip according to claim 46, including alignment means for angularly positioning said insertion tip in a specific orientation relative to a body cavity cleaning device.

53. An insertion tip according to claim 50, wherein said inlet chamber includes a discharge opening, said discharge opening being axially offset relative to a primary axis of a discharge opening of said insertion tip.

54. An insertion tip according to claim 50, wherein said inlet chamber includes a discharge opening, said discharge opening being narrow relative to the remainder of said inlet chamber and a discharge opening of said insertion tip.

55. An insertion tip according to claim 46, wherein said tip is made from an optically translucent material, permitting a user to visually ascertain the efficacy of a cleaning procedure.

* * * * *